US008790688B2

(12) United States Patent
Juel-Friis et al.

(10) Patent No.: US 8,790,688 B2
(45) Date of Patent: Jul. 29, 2014

(54) WOUND CARE DEVICE FOR LOCAL TREATMENT OF PAIN IN A WOUND

(75) Inventors: Gitte Juel-Friis, Horsholm (DK); Tine Richter-Friis, Nodebo (DK); Truels Sterm Larsen, Kobenhaven N (DK)

(73) Assignee: Coloplast A/S, Humlebaek (DK)

(*) Notice: Subject to any disclaimer, the term of this patent is extended or adjusted under 35 U.S.C. 154(b) by 1206 days.

(21) Appl. No.: 10/499,087

(22) PCT Filed: Dec. 19, 2002

(86) PCT No.: PCT/DK02/00884
§ 371 (c)(1),
(2), (4) Date: Jun. 16, 2004

(87) PCT Pub. No.: WO03/055536
PCT Pub. Date: Jul. 10, 2003

(65) Prior Publication Data
US 2005/0074486 A1  Apr. 7, 2005

(30) Foreign Application Priority Data

Dec. 21, 2001 (DK) .................. 2001 01942

(51) Int. Cl.
| A61L 15/16 | (2006.01) |
| A61L 15/42 | (2006.01) |
| A61L 15/44 | (2006.01) |
| A61P 17/00 | (2006.01) |
| A61P 17/02 | (2006.01) |

(52) U.S. Cl.
USPC ........... 424/447; 424/443; 424/445; 424/446; 514/18.6; 514/18.7

(58) Field of Classification Search
USPC ......... 514/54, 772; 424/45, 78, 422, 430, 445
See application file for complete search history.

(56) References Cited

U.S. PATENT DOCUMENTS

| 4,231,369 A | 11/1980 | Sorensen et al. |
| 4,367,732 A | 1/1983 | Poulsen et al. |
| 4,590,212 A | 5/1986 | Bernstein ................... 514/629 |
| 4,627,429 A * | 12/1986 | Tsuk ............... 604/307 |
| 5,051,259 A | 9/1991 | Olsen et al. |
| 5,322,683 A * | 6/1994 | Mackles et al. .................. 424/45 |
| 5,389,092 A | 2/1995 | Guillemet et al. ............. 604/304 |
| 5,527,534 A * | 6/1996 | Myhling ..................... 424/430 |
| 5,643,187 A | 7/1997 | Næstoft et al. |
| 5,693,624 A * | 12/1997 | Hardy et al. ..................... 514/54 |
| 5,714,225 A | 2/1998 | Hansen et al. |
| 5,716,621 A * | 2/1998 | Bello et al. .................... 424/443 |
| 5,719,197 A | 2/1998 | Kanios et al. |
| 5,744,151 A * | 4/1998 | Capelli ......................... 424/405 |
| 5,792,469 A | 8/1998 | Tipton et al. |
| 5,891,463 A * | 4/1999 | Bello et al. .................... 424/449 |
| 5,910,125 A * | 6/1999 | Cummings et al. ............. 602/58 |
| 5,910,489 A * | 6/1999 | Falk et al. ........................ 514/54 |
| 5,914,125 A * | 6/1999 | Andrews et al. .............. 424/443 |
| 5,916,918 A | 6/1999 | Konishi et al. .................. 514/546 |
| 5,993,849 A | 11/1999 | Assmus et al. |
| 6,048,850 A | 4/2000 | Young et al. |
| 6,190,689 B1 | 2/2001 | Hoffmann et al. |
| 6,190,690 B1 | 2/2001 | Park et al. |
| 6,277,401 B1 * | 8/2001 | Bello et al. .................... 424/449 |
| 6,312,713 B1 | 11/2001 | Korol et al. |
| 6,890,553 B1 * | 5/2005 | Sun et al. ....................... 424/449 |
| 2002/0028243 A1 * | 3/2002 | Masters ......................... 424/484 |

FOREIGN PATENT DOCUMENTS

| CA | 2 046 337 | 6/1991 |
| EP | 1046395 | 10/2000 |
| EP | 0693292 | 11/2001 |
| EP | 1120115 | 5/2003 |
| GB | 2 036 042 | 6/1980 |
| GB | 2 311 027 | 9/1997 |
| HU | 180013 | 1/1983 |
| HU | 206993 | 6/1992 |
| HU | 0003151 | 2/2001 |
| WO | 94/23713 | 10/1994 |
| WO | 97/46265 | 12/1997 |
| WO | 98/22114 | 5/1998 |
| WO | WO 99/64081 | * 12/1999 | .............. A61L 15/42 |
| WO | 00/02539 | 1/2000 |
| WO | 00/07574 | 2/2000 |
| WO | 01/80797 A1 | 11/2001 |
| WO | WO 01/87267 | * 11/2001 | ............... A61K 9/10 |

OTHER PUBLICATIONS

"Remington: The Science and Practice of Pharmacy," (1995) A.R Gennaro Editor, Mack Publishing, Phila. PA.*
Merriam-Webster Online Dictionary website: http://www.merriam-webster.com/dictionary/integral; for the term: integral.*

(Continued)

Primary Examiner — Robert A Wax
Assistant Examiner — Jeffrey T Palenik
(74) Attorney, Agent, or Firm — Coloplast Corp., Coloplast A/S; Nick Baumann

(57) ABSTRACT

A wound care device for local treatment of pain in a wound is provided. The device comprises an active pain relieving composition, which can also be an anti-inflammatory agent. The wound care device is suitable for treatment of pain in open wounds. The device can include small amounts of pain relieving compositions that are effective in relieving pain at the wound while not resulting in any systemic effects. The device may be in the form of a wound dressing, and the pain relieving composition may be delivered to the wound through a controlled release system.

72 Claims, No Drawings

(56) References Cited

OTHER PUBLICATIONS

Merriam-Webster Online Dictionary website: http://www.merriam-webster.com/dictionary/wound; for the term: wound.*

Smith, I. et al., "Secondary Tonsillectomy Haemorrhage and Non-Steroidal Anti-Inflammatory Drugs", Journal of Laryngology and Otology, vol. 113, pp. 28-30, Jan. 1999.

Spell, N., "Stopping and Restarting Medications in the Perioperative Period", Medical Clinics of North America, vol. 85, No. 5, pp. 1117-1128, Sep. 2001.

Jones, M.K., et al., "Inhibition of Angiogenesis by Non-Steroidal Anti-Inflammatory Drugs", Nature Medicine, vol. 5, No. 12, pp. 1418-1422, Dec. 1999.

Abd-El-Aleem, S.A., et al., "Expression of Cyclooxygenase Isoforms in Normal Human Skin and Chronic Venous Ulcers", Journal of Pathology, 195, pp. 616-623, 2001.

Hunt, T.K., et al., "Physiology of Wound Healing", Advances in Skin & Wound Care, vol. 13, Supp. 2, pp. 6-11, May/Jun. 2000.

Stotts, N., et al., "Chronic Wound Care: Co-Factors in Impaired Wound Healing", Health Management Publications, pp. 64-72, 1997.

Bolton, L.L., et al., "Topical Medications and Pharmacological Agents in Wound Healing", Clinical Wound Management, pp. 55-72, 1995.

Dvivedi, S., et al., "Effect of Ibuprofen and Diclofenac Sodium on Experimental Wound Healing", Indian Journal of Experimental Biology, vol. 35, pp. 1243-1245, Nov. 1997.

Fang, C., et al., "Failure of Topical Prostaglandin Inhibitors to Improve Wound Healing following Deep Partial-Thickness Burns", Journal of Trauma, vol. 23, No. 4, pp. 300-305, Apr. 1983.

Briggs, M., et al., "Topical Agents or Dressings for Pain in Venous Leg Ulcers", Cochrane Library Document, pp. 1-20, last updated May 24, 1999.

Harding, K., "Minimising Pain at Wound Dressing-Related Procedures", Principles of Best Practice, pp. 1-10, 2004.

Statement by Keith Harding with Curriculum Vitae, dated May 20, 2005.

Statement by Tonny Karlsmark with Curriculum Vitae, dated May 18, 2005.

Decision of EPO Board of Appeal, App. No. 96100581.6, Dec. 7, 2004.

EPO Opposition filed by Paul Hartmann AG on Aug. 23, 2006.

Co-Factors in Impaired Wound Healing, Nancy A. Stotts, pp. 64-72, dated 1997.

Topical Medications and Pharmacological Agents in Wound Healing, Laura L. Bolton, PhD, et al., Chapter 4, pp. 55-71, dated Jan. 1995.

Secondary tonsillectomy haemorrhage and non-steroidal anti-inflammatory drugs, I. Smith, F.R.C.S., et al., pp. 28-30, dated Jan. 1999.

* cited by examiner

WOUND CARE DEVICE FOR LOCAL TREATMENT OF PAIN IN A WOUND

This is a nationalization of PCT/DK02/00884 filed Dec. 19, 2002, and published in English.

FIELD OF THE INVENTION

This invention relates to wound care devices comprising an active pain-relieving agent for local pain relief in an open wound setting and a method of treating pain in such wounds.

BACKGROUND OF THE INVENTION

It is widely recognised that wound pain is one of the major problems associated with wounds or ulcers. Wounds are by definition divided into two categories: Acute and chronic wounds. Acute wounds may be wounds such as burns and surgical wounds, while chronic wounds may be in the form of pressure sores, leg ulcers and diabetic ulcers. Pain can be associated with both chronic and acute wounds although the influence on patients well-being will be more pronounced when the wound is chronic.

Pain can be divided into three categories: Acute pain, non-malignant pain and cancer pain. Wound pain will often be either acute or non-malignant dependent on the character of the actual wound and whether the wound is being manipulated or not e.g. during a dressing change. Furthermore, the pain will in general have nociceptive or neurogen origin.

Furthermore, wound pain can be sub-divided into three classes: Non-cyclic acute wound pain, which may occur during for instance at debridement of necrotic tissue in a wound or removal of drainage;

Cyclic acute wound pain, which may occur during for instance dressing changes or in some cases debridement; and Chronic wound pain, which is a persistent pain that can occur even without manipulation of the involved skin or tissue, i.e. pain between dressing changes.

In the following we will primarily address relief of the persistent pain or the chronic pain associated with wounds between dressing changes. However, treatments suitable for this purpose may also be able to relieve pain during dressing change and debridement as described below.

Pain in itself is of course a major discomfort for the patient and will therefore affect patients quality of life. In addition, pain stimulates catecholamine release and as a result of that local vasoconstriction arises and a reduced oxygen supply to a cutaneous wound will occur. This may affect wound healing and resistance to infection of the wound. Furthermore, wound healing may also be delayed due to the general influence pain may have on the patient, such as loss of appetite, less mobility, worse overall condition and lack of enthusiasm. However, the possible effect of pain on wound healing has not been proven in the literature and is therefore speculative. In contrast, it is well recognized that pain has an impact on the health related quality of life (HQOL) for patients.

Wound pain has proven to be decreased by modern moist wound healing principles. Moist wound healing dressings keep the environment under the dressing moist but are at the same time capable of absorbing considerable amounts of exudate from the wound, in order to protect the periulcer skin and to avoid leakage. During the wear time of a moist wound healing dressing, tissue and nerve endings remain moist. Such dressings, e.g. hydrocolloid dressings will be soothing and less painful than traditional dry gauze dressings during application and in situ. Debridement will often also be less painful as the wound bed will be kept in a moist condition and thus no painful drying out is seen.

Although moist wound healing has been proven to improve healing rates, relieve pain in situ, prevent the wound bed from drying out, decrease the discomfort with wound debridement, and overall, improve the quality of life for the patient, added benefits, in terms of a more direct way of addressing the local wound pain between dressing changes associated with wounds is still needed.

It is well known in the art to incorporate analgesics or anaesthetics into topical products for treatment of pain or to produce anaesthesia in intact skin surfaces or systemically in the body. These products may be in the form of trans-dermal dressings or patches, creams, gels or ointments. In order to enhance the rate at which the drug passes through the skin to reach the systemic circulation from e.g. the trans-dermal patch or to achieve an appropriate formulation for intact skin surfaces it is often desirable or even necessary to incorporate other components. These components will interfere with an open wound setting in terms of producing possible irritation, sensibilisation or even toxicological effects in the open wound setting and to the often very fragile periulcer skin around the open wound.

In International Patent Application No. WO 94/23713 is disclosed a trans-dermal anti-inflammatory compositions. The compositions may be used for topical and trans-dermal application, such as ointments and dressings and the anti-inflammatory composition is preferably NSAIDs (non-steroid anti-inflammatory drugs).

However, delivering drugs to intact healthy skin and to the systemic circulation is very different from delivering drugs locally to open wounds or damaged skin. The skin provides an effective barrier between the drug and the underlying tissue and blood circulation in trans-dermal delivery, and therefore, the drug has to be formulated in such a way that it is capable of overcoming this barrier. Also the concentration of the drug in the trans-dermal formulation has to be higher in order to overcome the skin barrier and reach the systemic circulation in a plasma concentration high enough for systemic effect. A wound is provided with little or no barrier, and furthermore, the wound will often exudate and may be contaminated.

Furthermore, a wound dressing often needs to be provided with wound exudates handling means, in order to give optimal comfort for the patient. The barrier for the release of the drug for local administration to an open wound will be the medical device, and not the intact skin. The medical device may absorb and retain the exudate from the wound, and therefore prevent the maceration of the surrounding skin and wound tissue that is often fragile and vulnerable. As a result, the wound management and patient comfort is increased. A trans-dermal patch, or a topical cream, or ointment will not be able to handle wound exudate. Neither the adhesive, nor the other components of the patch may be designed for an open wound setting and for contact with the very fragile skin surroundings. Also, the drug concentration in a trans-dermal system or a topical ointment, gel or cream may be too high to be used in an open wound where no absorption barrier is seen. Furthermore, additives such as penetration enhancers, comprised in the creams, gels or ointments or trans-dermal patches will make them unsuitable for use in an open wound, as these additives often are too aggressive, or even toxic for introducing directly into an open wound.

Most wound care products are prepared without such additives as these additives may interfere with the wound healing and influence the well being of the patient. Examples are hydrogels made especially for e.g. debridement in open wounds and for application under a dressing and other devices for moist wound healing like dressings comprising foams, alginates or hydrocolloids.

A controlled release of drugs is often desired both in trans-dermal delivery and open wound treatment. However, the release mechanisms may be quite different in the two systems. In a trans-dermal device such as a patch, cream, ointment or gel, the skin barrier may serve as the controlling release layer. The additives may further control the release. In a wound care device, the release may be controlled in other ways, e.g. by the amount of exudate from the wound, or by using controlled release matrices.

Analgesics generally can relieve pain in open wounds without seriously interfering with the sense perception. In contrast, anesthetics interfere with sense perception when applied locally, and can result in loss of consciousness when used systemically. Loss of sense perception in a wound and surroundings is considered to be not acceptable because the patient loses the ability to feel possible injury and change in the wound. Therefore it may be preferred to use analgesics in order to relieve wound pain over a longer period.

In U.S. Pat. No. 6,312,713 is disclosed a thin-layered dressing for surface wounds which gradually releases drugs, such as analgesics. The drug is incorporated in a hydrophilic polymeric matrix and may be used topically. The dressing is thin and does not comprise wound exudates handling means, and will thus only be suitable for dry wounds.

U.S. Pat. No. 5,792,469 a in situ forming film dressing with therapeutic agents such as pain relieving agents. The film is sprayed onto the desired body part. The dressing is only suitable for dry wounds, as no wound exudates handling means are included.

In U.S. Pat. No. 6,048,850 is disclosed a method of selectively inhibiting PGHS-2 in a human host. The reference is silent with respect to local wound treatment.

U.S. Pat. No. 6,190,689 discloses a trans-dermal device comprising a hot-melt adhesive with an incorporated substance. The use of pain relieving agents in the treatment of wounds is mentioned, but the reference is silent with respect to any details or examples to this subject.

In International Patent Application No. WO 00/07574 is disclosed medicinal products with retarded pharmacological activity. The products are primarily intended for use in catheters, though use in wound care devices is mentioned.

Thus, there is still a need for a medical device addressing superior wound management as well as local pain relief in terms of addition of analgesic compounds. Such a wound care device is achieved by the present invention combining the beneficial effects of moist wound healing with the pharmacological effects of a pain relieving agent, that supply pain relief locally to a wound and nearby surroundings but not systemically i.e. in the body.

BRIEF DESCRIPTION OF THE INVENTION

The present invention relates to a wound for dressing for local treatment of pain in a wound, said dressing comprising an absorbent element and an active pain relieving composition.

The present invention further relates to a wound care device for treatment of pain in a wound comprising an active pain relieving composition.

The invention yet further relates to a method of treating pain at a wound site.

DETAILED DESCRIPTION OF THE INVENTION

The present invention relates to a wound dressing for local treatment of pain in a wound, said dressing comprising an absorbent element and an active pain relieving composition, the dressing being constructed in such a manner that an anti-inflammatory pain killing agent in said composition is released to the wound at such a low rate that substantially no effective systemic plasma concentration of the pain killing agent can be found.

Furthermore, the present invention relates to a wound care device for local treatment of pain in a wound. The device includes an active pain relieving composition with an anti-inflammatory pain killing agent, the agent being released such that the amount of pain killing agent in the device is below the systemic or topical daily unit dose for systemic treatment using the agent.

In one embodiment of the invention the amount of pain killing agent is less than 75% of the systemic or topical daily unit dose for systemic treatment using the agent.

In another embodiment of the invention the amount of pain killing agent is less than 50% of the systemic or topical daily unit dose for systemic treatment using the agent.

It may be preferred that the amount of pain killing agent is less than 25% of the systemic or topical daily unit dose for systemic treatment using the agent.

It is even more preferred that the amount of pain killing agent is less than 10% of the systemic or topical daily unit dose for systemic treatment using the agent.

In one embodiment of the invention the amount of pain killing agent is less than 5% of the systemic or topical daily unit dose for systemic treatment using the agent.

The term systemic or topical daily unit dose for systemic treatment for a pain killing agent means the daily dose for achieving a systemic pain reliving effect, i.e. achieving a desired plasma concentration in a patient.

In Table 1 is shown examples of systemic or topical daily unit doses of various pain killing agents. Examples are shown below in the range of normally recommended use for adults:

TABLE 1

| Drug | Systemic daily unit dose | Topical daily unit dose |
| --- | --- | --- |
| Naproxen | 200–500 mg | Not available |
| Ketoprofen | 100–300 mg | 375 mg |
| Piroxicam | 10–20 mg | 25 mg |
| Ibuprofen | 1200–2400 mg | 500–800 mg |
| Celecoxib | 200–400 mg | Not available |
| Acetylsaliclylic acid | 2–4 g | Not available |
| Indomethacin | 150–200 mg | Not available |
| Acetaminophen | 2–4 g | Not available |
| Diclofenac | 150–200 mg | Not available |

The present invention discloses an approach for formulating a moist wound healing device with improved pain relieving properties. The moist wound healing principles offers a passive pain relieving effect by keeping the wound moist. The addition of an active pain relieving composition to the wound care device further improves the capability of the device of relieving wound pain especially the persistent pain or chronic pain between dressing changes.

The analgesics in the device of the invention may be released over time locally to the wound. Preferably, the release of the pain relieving composition is so low that no systemic effect is seen. Thus, the concentration of analgesics in the device of the invention may be so low that little or no effective systemic plasma concentration can be found. This will reduce or even eliminate the possible systemic side effects of the analgesics, and at the same time provide the patient with maximum safety, as oral doses or topical doses on intact skin can be taken at the same time. Thus, the device renders it possible to ingest additional medication, if needed, orally or topically of the same type as in the wound care device, without the risk of overdosing. Furthermore, side effects are lowered and compliance will be better as well as the HQoL.

For different analgesics, the plasma concentration for systemic effect in the lowest range is reported to be as follows given as examples: Acetylsalicylic acid: 270 µg/ml; Ketoprofen: 3 µg/ml; Ibuprofen: 10 µg/ml; Piroxicam: 1 µg/ml. Thus, a wound care device for treatment of pain in a wound releasing analgesics locally to a wound site may be designed in such a way that the plasma concentration is under the lowest range for systemic effect in the body.

This is also true for other anti-inflammatory pain reliving compositions being suitable for incorporation into medical devices combining wound exudates handling means and local treatment of wound pain in open wounds.

It is widely held that anti-inflammatory pain killing agents, such as NSAIDS, are unsuitable for use in open wound settings. The compositions are primarily used for treatment of systemic diseases, not for local treatment. It is further believed that the compositions may cause local irritation, as well as it has been recommended to avoid use of such compositions in open wounds.

It has surprisingly been found that by incorporating an anti-inflammatory pain killing agent in a wound care device, a local pain-relieving effect in an open wound is achieved. Local side effects have surprisingly not been seen as well as the plasma concentrations, if any, of the agent were below the concentrations for systemic effect.

The device according to the present invention is primarily intended for use as local pain relief. When a systemic effect of the pain-relieving agent is desired e.g. when providing pain relief against rheumatoid arthritis, muscle pain or headaches, orally ingested analgesics may be preferred. The pain relieving composition of the device of the invention may be applied to damaged skin locally and directly onto an open wound without interfering with the wound healing.

Prostaglandins, leukotrienes, and thromboxanes are key inflammatory mediators produced from arachidonic acid. Inhibition of the synthesis of these mediators is the target of the most highly prevalent class of anti-inflammatory drugs, the NSAIDs. Inflammatory mediators will stimulate pain nociceptors and as a result pain is produced.

Pain impulses in skin tissue arise from pain receptors in the skin and deeper structures. The intensity of the pain increases when the number of receptors activated and the frequency of impulses increase. The perception of pain in e.g. peripheral tissue such as the skin begins with stimulation of nerve fibres called nociceptors. In a process called transduction, a nociceptive stimulus makes nociceptor membranes permeable to sodium ions. In a second process known as transmission, the influx of sodium ions sends a signal to the dorsal horn of the spinal cord. In a third process, modulation, systems that inhibit and facilitate pain act on the generated signals. Finally in the perception process a factor called plasticity, which is based in part on prior experienced pain, determines how intensely the pain is perceived. Pain is therefore also subjective. It has both a psychological and physiological component. Acute, and social, cultural and psychological factors affect it. The feeling of pain is protective in situations where it alerts the body of actual or potential damage. Beyond these situations its function is less clear.

Inflammatory pain is believed to be important for the actually feeling of chronic or persistent wound pain. It is believed that tissue injury as e.g. seen in chronic wounds triggers the release of multiple inflammatory mediators that themselves, alter nociceptor function. The level of inflammation is therefore elevated and may be lowered by addition of anti-inflammatory drugs locally to the wound that would lead to pain relief.

Preferably the pain relieving composition comprises an anti-inflammatory painkilling agent that blocks the production of inflammatory mediators produced from arachidonic acid.

NSAIDs (non-steroid anti-inflammatory drugs) generally have analgesics and antipyretic properties along with their anti-inflammatory capabilities. Anti-inflammatory pain killing agents interact with enzyme targets such as cyclooxygenase-inhibiting NSAIDs. The enzymes PGHS (prostaglandin H synthease), commonly know as COX (cyclooxygenase), is responsible for processing arachidonic acid into inflammatory mediators. COX comes from two isoforms COX 1 and COX 2. COX 1 is produced in a more or less constant level at all times and is involved in forming the prostaglandins that perform several important functions, including protection of the gastric mucosa and support of renal function. Consequently, inhibitors of COX 1 may interfere with the gastric mucosa and renal function. COX 2, which is inducible, is expressed after tissue injury and promotes inflammation. Thus, selective inhibition of COX-2, with sparing of COX 1 activity, should be expected to block inflammation without gastric and renal side effects upon oral administration. However, use of COX 1 locally in an open wound setting will not produce any systemic side effects. Classical NSAIDs acts on both COX 1 and COX 2 whereas newer drugs work selectively on COX 2.

Thus, in one embodiment of the invention the pain relieving composition may be capable of inhibiting mediators responsible for processing arachidonic acid into inflammatory mediators.

In a preferred embodiment of the invention, the pain relieving composition may be capable of inhibiting COX 1 and COX 2.

In one embodiment of the invention the pain relieving composition may be capable of specifically inhibiting COX 2. The pain relieving composition may comprise one or more compounds chosen from the group of anti-inflammatory compositions such as Phenylpropionic acids, Phenelacetic acids, indoleacetic acids, Pyrroleacetic acids, N-Phenylacetic acids, Salicylates, Enolic acids, Phenols, Non-acids or Coxibs.

Examples of such compounds for the pain relieving composition may be: Propionic acid derivatives such as Naproxen, Ibuprofen, Ketoprofen, Fenoprofen, Flurbiprofen Dexibuprofen or Tiaprofenic acid, Acetic acid derivatives such as Diclofenac, Alclofenac, Fenclofenac, Etodolac, Aceclofenac, Sulindac or Indomethacin, Pyrroleacetic acids such as Ketorolac or Tolmetin, N-Phenylacetic acids such as Mefenamic acid, Salicylates such as Acetyl salicylic acid (Aspirin), Salicylic acid or Diffunisal, Pyrazolon derivatives such as Phenylbutazone, Oxicam derivatives such as Piroxicam, Tenooxicam, Meloxicam or Lornoxicam, Enolic acid derivatives Aminopyrene or antipyrene, Phenols such as Acetaminophen or Phenacetin, Non-acid derivatives Nabumeton, Coxib derivatives such as Celecoxib or Rofecoxib.

Compounds inhibiting COX 2 specifically may be Coxib derivatives such as Celecoxib or Rofecoxib.

In one embodiment of the invention the pain relieving composition is Ibuprofen.

In another embodiment of the invention the pain relieving composition is Ketoprofen.

The pain relieving composition may be incorporated as particles, coated particles or diluted in constituent phases of the medical device or distributed in an aiding agent therein.

The particles may be mixed with one or more of the constituents of the wound care device, such as the particles may be incorporated into an adhesive, an absorbent layer or they may be incorporated in a film.

The pain relieving composition may be dissolved or suspended in one or more of constituents of the wound care device or alternatively in one or more constituents acting as precursor material for the constituent.

In one embodiment of the invention the particles may be dissolved in an aiding vehicle in the form of a liquid or solid and may appear as a discrete phase in one or more of the components of the device, e.g. a water insoluble composition may be incorporated into an hydrophobic vehicle or vice versa.

The wound care device may further comprise a controlled release system.

The pain relieving effect of the device according to the invention is over time originated from release of the pain killing agent to the wound. When studying a dressing that has been applied over an open wound for a period, the pain killing agent diminish or disappear in the area directly over the wound due to a release to the wound, while a negligible amount will be released in the area over the periulcer skin.

In one embodiment of the invention the release may be controlled as a function of the amount of a selected constituent of the wound exudate.

In a preferred embodiment of the invention the selected constituent is liquid.

The pain relieving composition may be released to the wound by controlled release locally in relation to the amount of wound exudate absorbed and retained in the medical device and further delayed by coating the pain relieving agent or incorporating it into a vehicle.

In one embodiment of the invention the pain relieving component may be in the form of coated particles with controlled release properties. The coating may be any suitable coating known in the art of release systems providing the particles with the desired release properties. An example may be Ketoprofen particles coated with an Eudragit grade.

Preferably, the device of the invention is in the form of a wound dressing, or a part of a wound dressing.

The dressing may be in the form of a single unit or a layered product.

The device may comprise wound exudate absorbing means.

The dressing of the invention may comprise an absorbing constituent or element. The pain relieving composition may be comprised in such absorbing constituent or element as wound exudate or other liquid will then more easily be brought into contact with the pain relieving composition.

An absorbing constituent or element may preferably be a separate element of an absorbing foam, a hydrogel, or paste, hydro-sheet or be in the form of hydrocolloids and/or an alginate in the form of a separate element or particulate and homogeneously distributed in the dressing.

In one embodiment of the invention the absorbing element comprises foam, preferably polyurethane foam.

Such an absorbing element may in one embodiment constitute a dressing of the invention. In such case, the absorbing element may in itself show adhesive properties or it may not show adhesive properties and it will then typically be secured to the desired site using conventional means such as a cover dressing.

The device of the invention may comprise an adhesive.

The device of the invention may comprise a skin-contacting surface comprising an area showing a skin friendly adhesive.

Such a dressing may suitably be a dressing comprising a substantially water-impervious layer or film and a skin-friendly adhesive in which an absorbing constituent or element is incorporated.

The skin-friendly adhesive may be any skin-friendly adhesive known per se, e.g. an adhesive comprising hydrocolloids or other moisture absorbing constituents such as the adhesives disclosed in U.S. Pat. No. 4,231,369 and in U.S. Pat. No. 4,367,732 comprising hydrocolloids. A dressing comprising a separate absorbing element may e.g. be of the type disclosed in U.S. Pat. No. 5,051,259 or 5,714,225.

A water impervious layer or film may be of any suitable material known per se for use in the preparation of wound dressings e.g. a foam, a non-woven layer or a polyurethane, polyethylene, polyester or polyamide film. A suitable material for use as a water impervious film is a polyurethane such as the low friction film material is disclosed in U.S. Pat. No. 5,643,187.

In another embodiment of the invention the device may be a wound cavity filler. The cavity filler may e.g. be in the form of fibres, gel or hydrogel, foam or powder.

The device of the invention may further comprise one or more active ingredients besides the pain killing agent.

The wound care device according to the invention may comprise one or more active ingredients, e.g. a pharmaceutical medicament. Examples of such pharmaceutical medicaments such as bacteriostatic or bactericidal compounds, e.g. iodine, iodopovidone complexes, chloramine, chlorohexidine, silver salts such as sulphadiazine, silver nitrate, silver acetate, silver lactate, silver sulphate, silver sodium thiosulphate or silver chloride, zinc or salts thereof, metronidazol, sulpha drugs, and penicillin's, tissue-healing enhancing agents, e.g. RGD tripeptides and the like, proteins, amino acids such as taurine, vitamins such ascorbic acid, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, emollients, retinoids or agents having a cooling effect which is also considered an aspect of the invention.

The active ingredient may also comprise odour controlling or odour reducing material such as charcoal.

The invention further relates to a method of treating pain at a wound site comprising applying to the wound a wound care device comprising an active pain relieving composition.

The pain relieving composition may preferably be an anti-inflammatory pain relieving composition, said composition is an anti-inflammatory pain killing agent, wherein the amount of pain killing agent in the device is below the daily unit dose for systemic treatment or daily unit dose for topical treatment using the agent.

When applying a wound care device according to the invention to a wound, the pain relieving composition will be released to the wound bed, and pain relief is achieved. Preferably the pain relieving composition will be released over a period of time, in order to provide a controlled or sustained release of the composition. Thus, a prolonged wear time of the dressing is achieved, rendering it possible to avoid frequent dressing changes. Change of dressings is often associated with pain, hence a low frequency of dressing changes is desired.

EXAMPLES

Example 1

Preparation of a Foam Dressing

A polyurethane foam was prepared in the following way: 100 parts w/w Hypol2002 (Dow Chemical Company) were mixed with 1 part w/w Pluronic 62 (BASF), 100 parts w/w of water and an amount of the pain killing agent as specified in the following examples. The materials were mixed together for approximately 15 seconds. The liquid was poured into a mould and allowed to react for 10 minutes. The resulting foam sheet was dried in an oven at 70° C. for 30 minutes, and cut into 20×20 cm dressings with a thickness of 4.4 mm. The device may further be sterilized using gamma radiation.

Example 2

Foam Dressing Containing Ibuprofen

A foam dressing was prepared as described in Example 1 with 1 part w/w Ibuprofen.

Example 3

Foam Dressing Containing Piroxicam

A foam dressing was prepared as described in Example 1 with 0.04 part w/w piroxicam.

Example 4

Foam Dressing Containing Ketoprofen

A foam dressing was prepared as described in Example 1 with 0.06 part w/w ketoprofen.

Example 5

Preparation of a Hydrocolloid Dressing

A hydrocolloid adhesive was prepared from the following ingredients as described in U.S. Pat. No. 4,231,369: 25,1% Kraton D 1107 (Shell Chemical Company), 35.1% Arkon P90 (Arakawa Chemical), 30% Carboxy methyl cellulose, 8.8% dioctyladipat, 1% antioxidant (methylene-bis 4 methyl 6 t-butylphenol). The adhesive was coated in a layer of 1.1 mm on a polyurethane film, and the resulting laminate was cut into dressings with a size of 20×20 cm. The dressings were preferably sterilized by gamma irradiation.

Example 6

Hydrocolloid Dressing Containing Ibuprofen

A hydrocolloid dressing was prepared as described in Example 5 containing 97.8% w/w of the recipe and 2.2% w/w Ibuprofen was added.

Example 7

Hydrocolloid Dressing Containing Piroxicam

A hydrocolloid dressing was prepared as described in Example 5 containing 99.96% w/w of the recipe and 0.04% w/w Piroxicam was added.

Example 8

Hydrocolloid Dressing Containing Ketoprofen

A hydrocolloid dressing was prepared as described in Example 5 containing 99.6% w/w of the recipe and 0.4 w/w Ketoprofen was added.

Example 9

Preparation of a Hydrogel

A water containing hydrogen comprising the following ingredients was prepared: 96% w/w water, 3.6% w/w Aquasorb, 0.4% w/w Calcium alginate. About ⅔ of the water was added to a mixer. Calcium alginate and the pain killing agent was mixed, and thereafter ¼ of the Aquasorb was added first, followed by the rest of the Aquasorb. This mixture was slowly added to the water and mixed further. When the phase was homogenous, the rest of the water was added slowly with continuous mixing for at least 20 minutes. The gel may be sterilized using an autoclave.

Example 10

Preparation of a Hydrogel Containing Ketoprofen

A hydrogel was prepared as described in Example 9 containing 99.9% w/w of the recipe and 0.1% w/w Ketoprofen.

Example 11

Preparation of a Hydrogel Containing Ibuprofen

A hydrogel was prepared as described in Example 9 containing 98-99.5% w/w of the recipe and 0.5-2.0% w/w Ibuprofen.

Example 12

Preparation of a Hydrogel Containing Piroxicam

A hydrogel was prepared as described in Example 9 containing 99.9% w/w of the recipe and 0.1% w/w Piroxicam.

Example 13

Use of a Dressing According to the Present Invention

A foam dressing as described in Example 1 and 2 was applied to patients with venous ulceration. The patients were treated for 10 days, with change of the dressing every second day. Very good local pain relief and a convincing reduction of the pain intensity during wear time of the dressing were reported. No local side effects as well as systemic side effects were observed. Plasma concentrations were monitored closely. No levels for systemic effect was found in plasma. Further it was shown that wound healing progressed according to expectations i.e. no delay in wound healing was observed. A very convincing improvement in HQoL was seen during the treatment time.

The invention claimed is:
1. A drug delivery device consisting of:
a) a polyurethane foam absorbing element;
b) a pain relieving composition selected from the group consisting of naproxen, ketoprofen, piroxicam, ibupro- fen, celecoxib, acetylsalicylic acid, indomethacin, acetaminophen and diclofenac, wherein
said pain relieving composition is provided in an effective amount sufficient to produce localized non-systemic pain relief; and
c) an adhesive, for securing the drug delivery device to a surface, the adhesive being separate and independent from the polyurethane foam absorbing element, wherein said pain relieving composition is incorporated into the polyurethane foam absorbing element and wherein the polyurethane foam absorbing element and pain relieving composition are provided in a dry state within the drug delivery device.

2. The drug delivery device of claim 1, wherein said pain relieving composition is ibuprofen.

3. The drug delivery device of claim 1, wherein said pain relieving composition is ketoprofen.

4. The drug delivery device of claim 1, wherein said pain relieving composition is diclofenac.

5. The drug delivery device of claim 1, wherein said pain relieving composition is naproxen.

6. The drug delivery device of claim 1, wherein said pain relieving composition is piroxicam.

7. The drug delivery device of claim 1, wherein said pain relieving composition is acetaminophen.

8. The drug delivery device of claim 1, wherein said pain relieving composition is acetylsalicylic acid.

9. The drug delivery device of claim 1, wherein said pain relieving composition is celecoxib.

10. The drug delivery device of claim 1, wherein said pain relieving composition is indomethacin.

11. A drug delivery device consisting of:
a) a polyurethane foam absorbing element;
b) a pain relieving composition containing ibuprofen;
c) the amount of said pain relieving composition is provided in an effective amount sufficient to produce localized non-systemic pain relief up to about 1200 mg; and
d) an adhesive for securing the drug delivery device to a surface, the adhesive being separate and independent from the polyurethane foam absorbing element, wherein said pain relieving composition is incorporated into the polyurethane foam absorbing element and wherein the polyurethane foam absorbing element and pain relieving composition are provided in a dry state within the drug delivery device.

12. The drug delivery device of claim 11, wherein said pain relieving composition is ibuprofen in an effective amount of up to about 900 mg.

13. The drug delivery device of claim 11, wherein said pain relieving composition is ibuprofen in an effective amount of up to about 600 mg.

14. A drug delivery device consisting of:
a) a polyurethane foam absorbing element;
b) a pain relieving composition selected from the group consisting of naproxen, ketoprofen, piroxicam, ibuprofen, celecoxib, acetylsalicylic acid, indomethacin, acetaminophen and diclofenac wherein
said pain relieving composition is provided in an effective amount sufficient to produce localized non-systemic pain relief; and
c) a water impervious layer, wherein the polyurethane foam absorbing element is coated in the water impervious layer, wherein
said pain relieving composition is incorporated into the polyurethane foam absorbing element and wherein the polyurethane foam absorbing element and pain relieving composition are provided in a dry state within the drug delivery device.

15. The drug delivery device of claim 14, wherein said pain relieving composition is ibuprofen.

16. The drug delivery device of claim 14, wherein said pain relieving composition is naproxen.

17. The drug delivery device of claim 14, wherein said pain relieving composition is ketoprofen.

18. The drug delivery device of claim 14, wherein said pain relieving composition is piroxicam.

19. The drug delivery device of claim 14, wherein said pain relieving composition is celecoxib.

20. The drug delivery device of claim 14, wherein said pain relieving composition is acetylsalicylic acid.

21. The drug delivery device of claim 14, wherein said pain relieving composition is indomethacin.

22. The drug delivery device of claim 14, wherein said pain relieving composition is acetaminophen.

23. The drug delivery device of claim 14, wherein said pain relieving composition is diclofenac.

24. A drug delivery device consisting of:
a) a polyurethane foam absorbing element;
b) a pain relieving composition selected from the group consisting of naproxen, ketoprofen, piroxicam, ibuprofen, celecoxib, acetylsalicylic acid, indomethacin, acetaminophen and diclofenac;
wherein said pain relieving composition is provided in an effective amount sufficient to produce localized non-systemic pain relief, wherein
said pain relieving composition is incorporated into the polyurethane foam absorbing element; and
a securing component separate and independent from the polyurethane foam absorbing element and wherein the polyurethane foam absorbing element and pain relieving composition are provided in a dry state within the drug delivery device.

25. The drug delivery device of claim 24, wherein the pain relieving composition contains diclofenac,
the amount of said pain relieving composition being in an effective amount sufficient to produce a local pain-relieving effect in a wound up to about 150 mg.

26. The drug delivery device of claim 25, wherein said pain relieving composition is diclofenac in an effective amount sufficient to produce a local pain-relieving effect in a wound up to about 112 mg.

27. The drug delivery device of claim 25, wherein said pain relieving composition is diclofenac in an effective amount sufficient to produce a local pain-relieving effect in a wound up to about 75 mg.

28. The drug delivery device of claim 24, wherein the pain relieving composition contains ketoprofen,
said pain relieving composition being in an effective amount sufficient to produce a local pain-relieving effect in a wound up to about 100 mg.

29. The drug delivery device of claim 28, wherein said pain relieving composition is ketoprofen in an effective amount sufficient to produce a local pain-relieving effect in a wound up to about 75 mg.

30. The drug delivery device of claim 28, wherein said pain relieving composition is ketoprofen in an effective amount sufficient to produce a local pain-relieving effect in a wound up to about 50 mg.

31. The drug delivery device of claim 24, wherein the pain relieving composition contains naproxen;

said pain relieving composition being in an effective amount sufficient to produce a local pain-relieving effect in a wound up to about 200 mg.

32. The drug delivery device of claim 31, wherein said pain relieving composition is naproxen in an effective amount sufficient to produce a local pain-relieving effect in a wound up to about 150 mg.

33. The drug delivery device of claim 31, wherein said pain relieving composition is naproxen in effective an amount sufficient to produce a local pain-relieving effect in a wound up to about 100 mg.

34. The drug delivery device of claim 24, wherein the pain relieving composition contains piroxicam,
said pain relieving composition being in an effective amount sufficient to produce a local pain-relieving effect in a wound up to about 10 mg.

35. The drug delivery device of claim 34, wherein said pain relieving composition is piroxicam in an effective amount sufficient to produce a local pain-relieving effect in a wound up to about 7.5 mg.

36. The drug delivery device of claim 34, wherein said pain relieving composition is naproxen in an effective amount sufficient to produce a local pain-relieving effect in a wound up to about 5 mg.

37. The drug delivery device of claim 24, wherein the pain relieving composition contains acetaminophen,
said pain relieving composition being in effective an amount sufficient to produce a local pain-relieving effect in a wound up to about 2000 mg.

38. The drug delivery device of claim 37, wherein said pain relieving composition is acetaminophen in an effective amount sufficient to produce a local pain-relieving effect in a wound up to about 1500 mg.

39. The drug delivery device of claim 37, wherein said pain relieving composition is acetaminophen in an effective amount sufficient to produce a local pain-relieving effect in a wound up to about 1000 mg.

40. The drug delivery device of claim 24, wherein the pain relieving composition contains acetylsalicylic acid,
said pain relieving composition being in an effective amount sufficient to produce a local pain-relieving effect in a wound up to about 2000 mg.

41. The drug delivery device of claim 40, wherein said pain relieving composition is acetylsalicylic acid in an effective amount sufficient to produce a local pain-relieving effect in a wound up to about 1500 mg.

42. The drug delivery device of claim 40, wherein said pain relieving composition is acetylsalicylic acid in an effective amount sufficient to produce a local pain-relieving effect in a wound up to about 1000 mg.

43. The drug delivery device of claim 24, wherein the pain relieving composition contains celecoxib,
said pain relieving composition being in an effective amount sufficient to produce a local pain-relieving effect in a wound up to about 200 mg.

44. The drug delivery device of claim 43, wherein said pain relieving composition is celecoxib in an effective amount sufficient to produce a local pain-relieving effect in a wound up to about 150 mg.

45. The drug delivery device of claim 43, wherein said pain relieving composition is celecoxib in an effective amount sufficient to produce a local pain-relieving effect in a wound up to about 100 mg.

46. The drug delivery device of claim 24, wherein the pain relieving composition contains indomethacin,
said pain relieving composition being in an effective amount sufficient to produce a local pain-relieving effect in a wound up to about 150 mg.

47. The drug delivery device of claim 46, wherein said pain relieving composition is indomethacin in an effective amount sufficient to produce a local pain-relieving effect in a wound up to about 112 mg.

48. The drug delivery device of claim 46, wherein said pain relieving composition is naproxen in an effective amount sufficient to produce a local pain-relieving effect in a wound up to about 75 mg.

49. The drug delivery device of claim 24, wherein said pain relieving composition is ibuprofen.

50. The drug delivery device of claim 24, wherein said pain relieving composition is naproxen.

51. The drug delivery device of claim 24, wherein said pain relieving composition is ketoprofen.

52. The drug delivery device of claim 24, wherein said pain relieving composition is piroxicam.

53. The drug delivery device of claim 24, wherein said pain relieving composition is celecoxib.

54. The drug delivery device of claim 24, wherein said pain relieving composition is acetylsalicylic acid.

55. The drug delivery device of claim 24, wherein said pain relieving composition is indomethacin.

56. The drug delivery device of claim 24, wherein said pain relieving composition is acetaminophen.

57. The drug delivery device of claim 24, wherein said pain relieving composition is diclofenac.

58. A method of locally treating the pain caused by a wound, which comprises:
(1) providing a drug delivery device consisting of:
a) a polyurethane foam absorbing element; and
b) an effective amount of a pain relieving composition incorporated into the polyurethane foam absorbing component and selected from the group consisting of naproxen, ketoprofen, piroxicam, ibuprofen, celecoxib, acetylsalicylic acid, indomethacin, acetaminophen and diclofenac, wherein the polyurethane foam absorbing element and pain relieving composition are provided in a dry state within the drug delivery device; and
(2) applying said drug delivery device to a wound to release said pain relieving composition into the wound in an amount effective to produce a local pain relieving effect in the wound.

59. The method of claim 58, wherein said pain relieving composition is ibuprofen.

60. The method of claim 58, wherein said pain relieving composition is naproxen.

61. The method of claim 58, wherein said pain relieving composition is ketoprofen.

62. The method of claim 58, wherein said pain relieving composition is piroxicam.

63. The method of claim 58, wherein said pain relieving composition is celecoxib.

64. The method of claim 58, wherein said pain relieving composition is acetylsalicylic acid.

65. The method of claim 58, wherein said pain relieving composition is indomethacin.

66. The method of claim 58, wherein said pain relieving composition is acetaminophen.

67. The method of claim 58, wherein said pain relieving composition is diclofenac.

68. A drug delivery device consisting of:
a) a polyurethane foam absorbing element;

b) a pain relieving composition selected from the group consisting of naproxen, ketoprofen, piroxicam, ibuprofen, celecoxib, acetylsalicylic acid, indomethacin, acetaminophen and diclofenac;

wherein said pain relieving composition is provided in an effective amount sufficient to produce localized non-systemic pain relief, wherein said pain relieving composition is incorporated into the polyurethane foam absorbing element and wherein the polyurethane foam absorbing element and pain relieving composition are provided in a dry state within the drug delivery device, wherein:

(a) if the pain relieving composition is naproxen, it is present in an amount less than 125 mg;
(b) if the pain relieving composition is ketoprofen, it is present in an amount less than 75 mg;
(c) if the pain relieving composition is piroxicam, it is present in an amount less than 5 mg;
(d) if the pain relieving composition is ibuprofen, it is present in an amount less than 600 mg;
(e) if the pain relieving composition is celecoxib, it is present in an amount less than 100 mg;
(f) if the pain relieving composition is acetylsalicylic acid, it is present in an amount less than 1000 mg;
(g) if the pain relieving composition is indomethacin, it is present in an amount less than 50 mg;
(h) if the pain relieving composition is acetaminophen, it is present in an amount less than 1000 mg; and
(i) if the pain relieving composition is diclofenac, it is present in an amount less than 50 mg.

69. The drug delivery device of claim 68, wherein said pain relieving composition is ibuprofen.

70. A drug delivery device consisting of:
a) a polyurethane foam absorbing element, wherein the polyurethane foam absorbing element does not show adhesive properties;
b) a pain relieving composition selected from the group consisting of naproxen, ketoprofen, piroxicam, ibuprofen, celecoxib, acetylsalicylic acid, indomethacin, acetaminophen and diclofenac wherein said pain relieving composition is provided in an effective amount sufficient to produce localized non-systemic pain relief; wherein said pain relieving composition is incorporated into the polyurethane foam absorbing element and wherein the polyurethane foam absorbing element and pain relieving composition are provided in a dry state within the drug delivery device, wherein:

(a) if the pain relieving composition is naproxen, it is present in an amount less than 125 mg;
(b) if the pain relieving composition is ketoprofen, it is present in an amount less than 75 mg;
(c) if the pain relieving composition is piroxicam, it is present in an amount less than 5 mg;
(d) if the pain relieving composition is ibuprofen, it is present in an amount less than 600 mg;
(e) if the pain relieving composition is celecoxib, it is present in an amount less than 100 mg;
(f) if the pain relieving composition is acetylsalicylic acid, it is present in an amount less than 1000 mg;
(g) if the pain relieving composition is indomethacin, it is present in an amount less than 50 mg;
(h) if the pain relieving composition is acetaminophen, it is present in an amount less than 1000 mg; and
(i) if the pain relieving composition is diclofenac, it is present in an amount less than 50 mg and a securing component to secure the polyurethane foam absorbing element to a surface.

71. The drug delivery device of claim 70, wherein said pain relieving composition is ibuprofen.

72. A drug delivery device consisting of:
a) a polyurethane foam absorbing element; and
b) ibuprofen, said ibuprofen is present in an amount of less than 1.5 mg/cm$^2$, wherein said ibuprofen is incorporated into the polyurethane foam absorbing element and wherein the polyurethane foam absorbing element and ibuprofen are provided in a dry state within the drug delivery device.

* * * * *